(12) United States Patent
Osawa et al.

(10) Patent No.: US 7,189,363 B2
(45) Date of Patent: Mar. 13, 2007

(54) GAS DETECTOR

(75) Inventors: Norimasa Osawa, Inuyama (JP); Kazuto Hirai, Konan (JP); Yuichi Koyama, Aichi (JP)

(73) Assignee: NGK Spark Plug Co., Ltd., Nagoya (JP)

(*) Notice: Subject to any disclaimer, the term of this patent is extended or adjusted under 35 U.S.C. 154(b) by 804 days.

(21) Appl. No.: 10/443,736

(22) Filed: May 23, 2003

(65) Prior Publication Data

US 2003/0235516 A1 Dec. 25, 2003

(30) Foreign Application Priority Data

May 24, 2002 (JP) ............... P.2002-151054

(51) Int. Cl.
- *G01N 21/00* (2006.01)
- *G01N 27/00* (2006.01)
- *B32B 5/02* (2006.01)
- *B32B 27/04* (2006.01)
- *B32B 27/12* (2006.01)

(52) U.S. Cl. ............... 422/83; 422/93; 422/94; 422/95; 422/96; 422/97; 422/98; 422/100; 422/103; 422/104; 436/143; 436/181; 73/1.01; 73/1.02; 73/23.2; 73/23.31; 73/23.32

(58) Field of Classification Search ............... 422/83, 422/93, 94, 95, 96, 97, 98, 100, 103, 104; 436/143, 181; 73/1.01, 1.02, 23.2, 23.31, 73/23.32

See application file for complete search history.

(56) References Cited

U.S. PATENT DOCUMENTS 3,819,330 A * 6/1974 Creighton ............... 422/83
4,742,763 A * 5/1988 Holter et al. ............... 454/75
5,624,639 A 4/1997 Ariga et al.
6,548,023 B1 * 4/2003 Matsuo et al. ............... 422/83

FOREIGN PATENT DOCUMENTS

| DE | 19983611 T1 | 6/2002 |
|---|---|---|
| EP | 0779170 | 6/1997 |
| EP | 0779170 A2 | 6/1997 |
| JP | 7-55740 | 3/1995 |
| JP | 8-192617 | 7/1996 |
| JP | 09-274003 A | 10/1997 |
| JP | 2000-043547 A | 2/2000 |
| JP | 2000-043549 A | 2/2000 |
| JP | 2001-066282 | 3/2001 |
| JP | 2001-066282 A | 3/2001 |
| WO | WO 00/18599 | 4/2000 |

\* cited by examiner

*Primary Examiner*—Brian Sines
(74) *Attorney, Agent, or Firm*—Morgan, Lewis & Bockius, LLP

(57) ABSTRACT

Of a gas detector 100, a chamber 105 formed between a center cover 150 and a cover 160 is a part of an air flow channel AF. A first shielding plate 165 is provided in the chamber 105. Water droplets that have entered the chamber from a chamber entrance 103 with air hit and adhere to an entrance-opposed surface 165E of the first shielding plate 165. The water thus adhering to the surface is pushed by the air flowing along the entrance-opposed surface 165E and by gravity, to thereby advance downward. The water then drips downward and is accumulated on a bottom wall surface 105WD which serves as an upper surface of a bottom wall section 161WD. The water is pushed by the flow of air, to thereby advance toward a chamber exit 104. The water is then drained downward from the chamber exit 104.

7 Claims, 11 Drawing Sheets

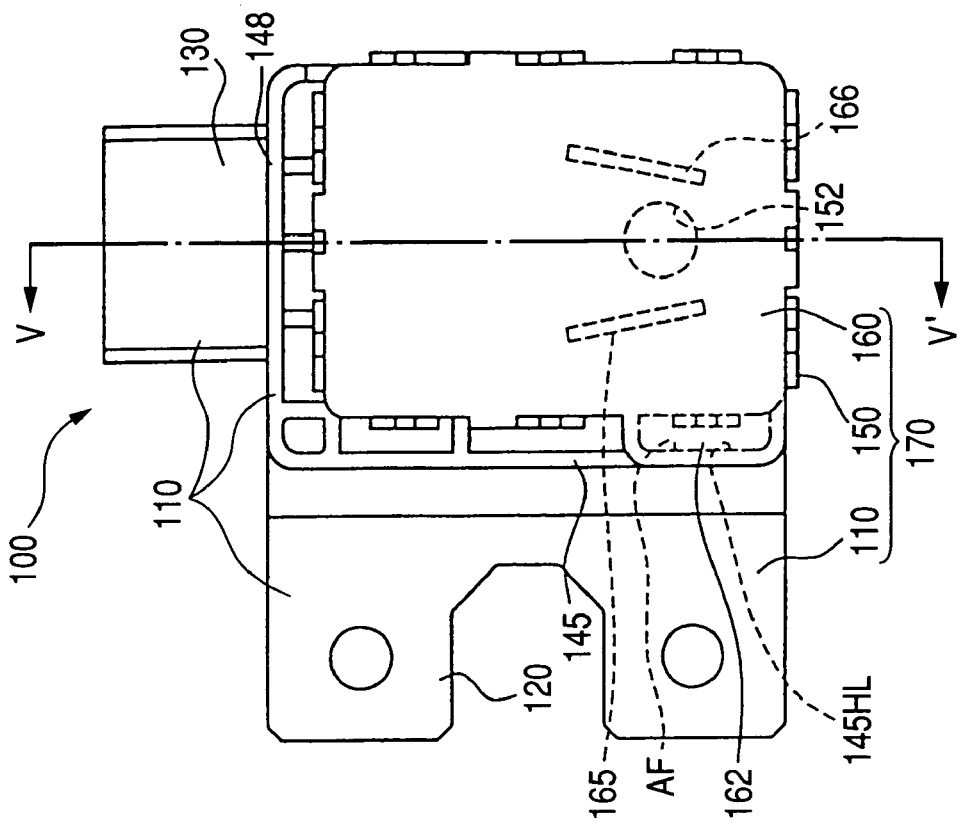
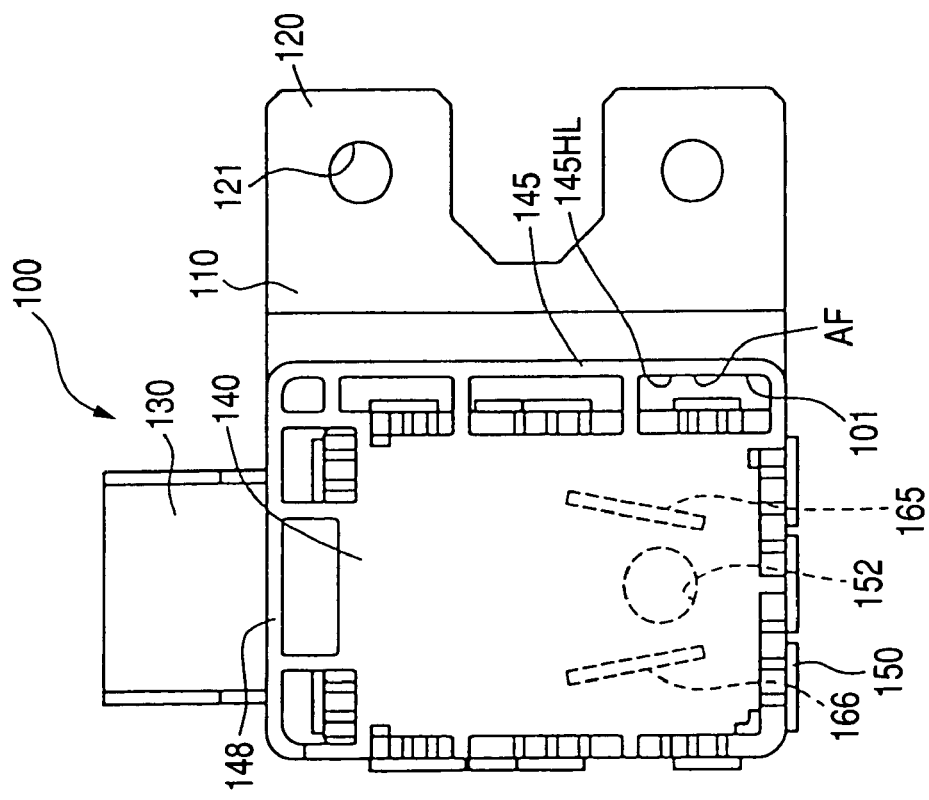

CROSS SECTION ALONG V-V'

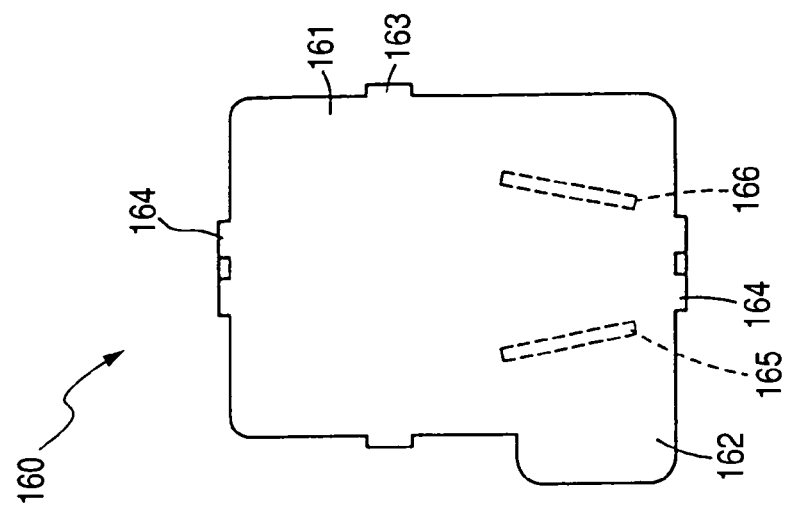
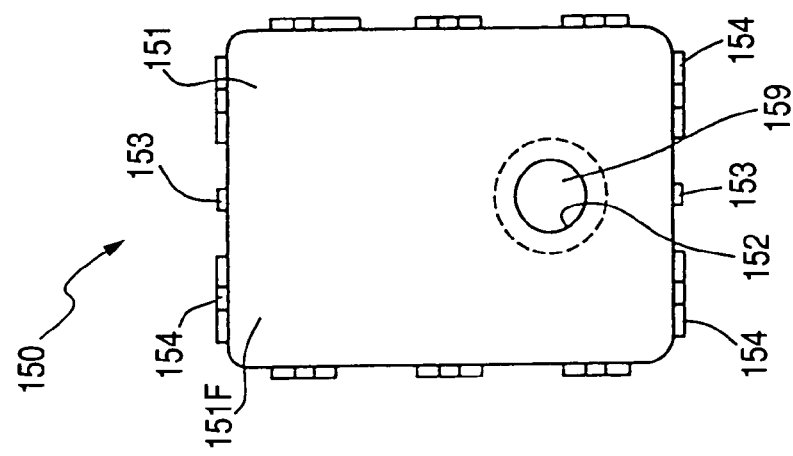
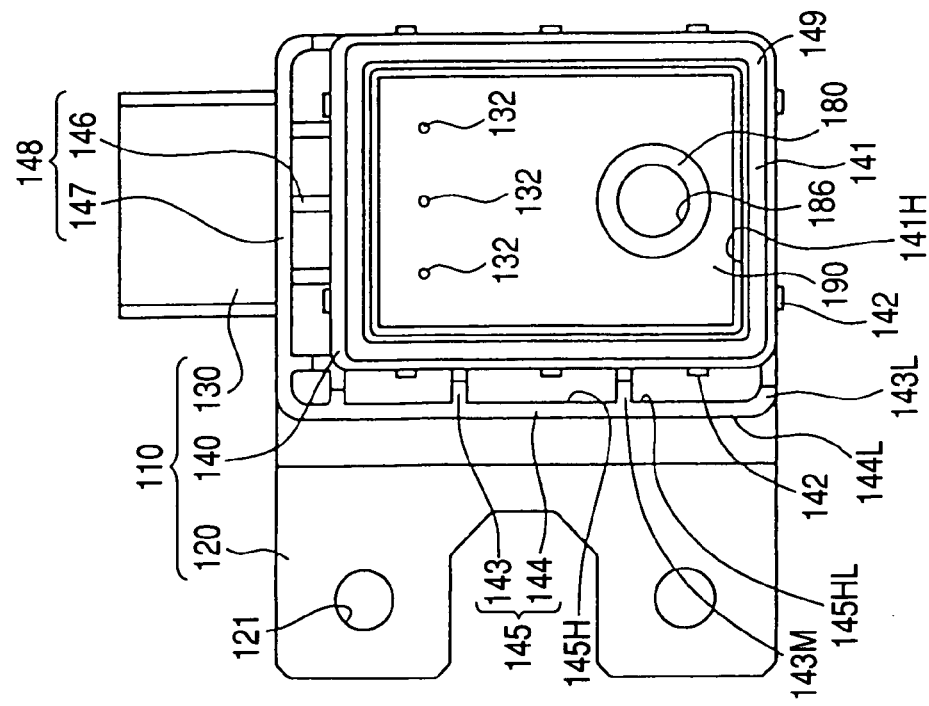

GAS DETECTOR

BACKGROUND OF THE INVENTION

The invention relates to a gas detector having a gas sensor for sensing a change in the concentration of a specific gas in air, and a case for housing the gas sensor.

Some gas detectors have a gas sensor incorporated in a case and detect a gas included in air flowing through an air flow channel formed in the case.

For example, a vehicle gas detector described in JP-A-8-192617 has a case. An air inlet port is formed in a lower portion of a front surface of the gas detector, and an air outlet port is formed in an upper portion of a rear surface of the detector. An air flow channel is formed in the case so as to extend upward from a substantially lower position. The gas sensor detects the concentration of a gas in the air flowing through the air flow channel. In the vehicle gas detector, the air having flowed into the air inlet port migrates upward along the air flow channel, whilst water droplets having flowed into the air inlet port in conjunction with the air adhere to a wall surface and migrate downward under the influence of gravity. The water droplets are then discharged out of the air inlet port.

In general, as a larger quantity of air flows through the air flow channel, the air present in the flow channel is replaced quickly, whereupon the response of the gas sensor becomes faster.

However, in relation to the vehicle gas detector, when an attempt is made to cause a larger quantity of air to flow into the detector by means of increasing the size of the air inlet port for taking in as large quantity of air as possible with a view toward increasing the response of the gas sensor, or by means of selecting the mount position of the gas detector, a large quantity of water droplets flow into the air flow channel in conjunction with air. In such a case, in the vehicle gas detector, air migrates upward along the air flow channel, and downward migration of water is hindered by flow of air. Thus, water cannot be discharged appropriately. Accordingly, water is accumulated within the air flow channel, thereby narrowing the air flow channel and hindering circulation of air. Thus, in some cases a drop in the response of the gas sensor has arisen. Moreover, if water is accumulated in the vicinity of the gas sensor, water may enter the gas sensor.

The invention has been conceived in view of the problems and is aimed at providing a gas detector which can discharge water appropriately even if air has flowed into the detector along with water droplets.

SUMMARY OF THE INVENTION

Means for resolution is a gas detector comprising: a case having an interior wall surface constituting a flow channel therein, through which air flows; and a gas sensor which is disposed in the case and detects a change in the concentration of specific gas in the air flowing through the flow channel, wherein, when the gas detector is disposed in a setup state, the case includes a chamber wall surface which constitutes a chamber occupying at least a portion of the flow channel belonging to the interior wall surface; and which includes a bottom wall surface for constituting a bottom surface of the chamber, a chamber entrance that is situated on a side of the chamber and opens toward an upstream portion of the flow channel, a chamber exit that is situated on a side of the chamber, opens toward a downstream portion of the flow channel, has a lower open edge remaining flush with or situated lower than the entrance of the chamber, and has a portion of the bottom wall surface taken as a portion of the open edge, and an air vent that is provided toward the exit of the chamber when viewed from the entrance of the chamber and at a position higher than the bottom wall surface and guides air to the gas sensor; and an entrance-side shielding member which is situated between the chamber entrance and the air vent, both belonging to the chamber; which shields the air vent when viewed from the entrance of the chamber; and which constitutes a first lower gap between the lowermost portion of the entrance-side shielding member and the bottom wall surface and circulates at least a portion of the air that has flowed into the chamber, wherein the bottom wall surface constitutes a horizontal plane or assumes a plate-like shape which becomes lower as the bottom wall surface approaches the exit of the chamber.

The gas detector of the invention has a chamber occupying at least a portion of a flow channel. The chamber has an entrance-side shielding member which shields an air vent when viewed from the entrance of the chamber. Hence, when fog-like or splashed water droplets have flowed into the chamber from the entrance thereof along with air, the fog-like or splashed water droplets are hindered by the entrance-side shielding member from advancing directly to the air vent. Therefore, the water droplets are prevented from coming into direct contact with the gas sensor that remains in communication with the air vent.

The water droplets that have come into collision with the entrance-side shielding member fall along the entrance-side shielding member under the influence of gravity and are accumulated on the bottom wall surface. The air vent is located at a position higher than the bottom wall surface, and hence further advancement of water into the air vent is prevented. When the bottom wall surface constitutes a horizontal surface, the water accumulated on the bottom wall surface is conveyed toward the exit of the chamber while being pressed by the air flowing through the first lower gap between the entrance-side shielding member and the bottom wall surface. Further, when the bottom wall surface has such a plane-like geometry that the bottom wall surface becomes lower as the bottom wall surface approaches the exit of the chamber, the water accumulated on the bottom wall surface is pressed by the air flowing through the first lower gap and also conveyed to the exit of the chamber by gravity. Specifically, the water that is accumulated on the bottom wall surface proceeds toward a downstream portion of the air flow channel. Further, the exit of the chamber takes the bottom wall surface as a portion of the opening edge. Hence, the water that has reached the exit of the chamber is readily discharged from the exit of the chamber.

Thus, when the air is flowing downstream through the air flow channel, the water accumulated on the bottom wall surface can be discharged from the exit of the chamber without returning to the entrance of the chamber, thereby preventing return of water to the entrance of the chamber (i.e., upstream) and occurrence of a hindrance in circulation of air. Further, water can be discharged efficiently by utilization of circulating force of air. Moreover, water can be discharged readily. Hence, circulation of a large quantity of air in the flow channel can be effected by means of increasing the size of the air inlet port of the flow channel of the gas detector. Hence, response of the gas sensor can be made quick.

Preferably, a portion of the gas detector is situated downstream with respect to the exit of the chamber with a water return prevention structure for preventing the water that has come out to a downstream part of the chamber from the chamber by way of the exit thereof from returning to the inside of the chamber by way of the exit of the chamber. The reason for this is that water in the chamber can be discharged without fail. As a result, the exit of the chamber also serves as a drain outlet. For example, as a water return prevention structure there may be mentioned a structure which does not employ any flow channel placed at a downstream position with respect to the exit of the chamber and in which drained water drops under influence of gravity, and a structure which employs a flow channel situated downstream from the exit of the chamber (i.e., a downstream flow channel), a bottom surface of the downstream flow channel being located lower than the lower end of the exit of the chamber.

Here, the expression "disposed in a setup state" means that the gas detector is arranged in the same state as that in which the gas detector is usually set up. For instance, in the case of a vehicle gas detector, the expression means that the upside/downside and inclination of the gas detector are set in the same manner as that achieved when the gas detector is attached to a body of a vehicle or the like.

Further, the expression "being located at a lower position" means that the relevant element is situated at a position lower than a horizontal level of a counterpart. Conversely, the expression "being located at a higher position" means that the relevant element is situated at a position higher than a horizontal level of a counterpart.

Moreover, the expression "air vent being shielded when viewed from the entrance of the chamber" means that the air vent is hidden behind the entrance-side shielding member and invisible from any angle from the entrance of the chamber. Here, the entrance-side shielding member may be formed integrally with the case or separately from the same.

Further, in relation to the gas detector, the wall surface of the chamber preferably includes an upper wall surface constituting an upper surface of the plate-like chamber; and the entrance-side shielding member preferably constitutes a first upper gap, through which at least a portion of the air having flowed into the chamber circulates, between the highest portion of the entrance-side shielding member and the upper wall surface.

According to the gas detector of the invention, a first lower gap and a first upper gap are formed above and below the entrance-side shielding member. Therefore, air circulates through the spaces located above and below the entrance-side shielding member. Hence, as compared with a case where the first upper gap is not provided, the air located in the vicinity of the air vent hidden behind the entrance-side shielding member of the chamber when viewed from the entrance thereof becomes more easily changeable, and hence the response of the gas sensor becomes faster.

In anyone of the foregoing gas detectors, at least either the gas-sensor-side air vent or the opposite-side air vent of the air vents is preferably coated with a filtering material which enables circulation of air but prevents circulation of water droplets.

In the gas detector, the air vents are coated with a filtering material, and hence adhesion of water droplets to the gas sensor by way of the air vents is prevented without fail.

In particular, the gas-sensor-side air vent is preferably coated with a filtering material. When viewed from the chamber, the filtering material is located at a deep position in the air vent. Hence, the chance of the filtering material being exposed directly to water is decreased, which is preferable.

In any of the gas detectors, the surface of the entrance-side shielding member opposing the entrance of the chamber preferably has such a geometry that a lower portion of the surface becomes distant from the entrance of the chamber.

When fog-like or spray-like water droplets have flowed into the chamber from the entrance thereof along with air, the fog-like or spray-like water droplets adhere to the surface of the entrance-side shielding member opposing the entrance after having entered the chamber from its entrance.

Here, when a lower portion of the surface opposing the entrance approaches closer to the entrance; specifically, when the surface opposing the entrance is oriented obliquely, the air migrates in an oblique upward direction over the surface. Hence, the air might hinder the water adhering to the surface from attempting to flow and fall under the influence of gravity or might push the water upward. For this reason, the water adhering to the surface is relatively less susceptible to discharge.

In contrast, the gas detector of the invention assumes the mode in which a lower portion of the surface opposing the entrance becomes far distant from the entrance of the chamber; more specifically, the lower portion being tilt downwardly. Hence, the air that has come into collision with this surface shifts direction toward an oblique downward direction along the surface. The air proceeds to the exit of the chamber while passing through the first lower gap. Hence, the water adhering to the surface opposing the entrance is also pushed by the flow of the air as well as by gravity, thereby advancing in an oblique downward direction. The water then falls down from the first gap existing between the bottom wall surface and the tilt surface. Thus, the water adhering to the surface opposing the entrance is caused to efficiently migrate to the exit of the chamber (i.e., a downstream side of the flow channel). Thus, the water adhering to the surface can be discharged efficiently.

The gas detector according to any one of the detectors set forth preferably further comprises:

an exit-side shielding member which is situated between the air vent of the chamber and the exit of the chamber; which shields the air vent when viewed from the exit of the chamber; and which constitutes a second lower gap between the lowermost section of the exit-side shielding member and the bottom wall surface and through which at least the air having flowed into the chamber circulates.

The gas detector of the invention also has the exit-side shielding member. Hence, even when the air flows backwardly from the exit of the chamber and when the fog-like or spray-like water droplets intrude into the chamber from it's exit, the exit-side shielding member hinders intrusion of the water droplets, so that the water droplets do not proceed directly to the air vent. Therefore, even when the air flows backward, arrival of the water droplets directly at the gas sensor that remains in communication with the air vent.

In the gas detector according to any one of the detectors set forth, a surface of the exit-side shielding member opposing the exit of the chamber preferably has such a geometry that a lower portion becomes distant from the exit of the chamber.

Even when the fog-like or spray-like water droplets have flowed into the chamber in conjunction with the air that has flowed backward into the chamber from the exit, the fog-like or spray-like water droplets adhere to the surface of the exit-side shielding member opposing the exit of the chamber when having entered the chamber from the exit thereof.

Here, the gas detector of the invention assumes a mode in which a lower portion of the surface opposing the exit becomes far distant from the entrance of the chamber; more specifically, the surface is downwardly oblique. Hence, the air that has come into collision with the surface advances after having shifted direction toward a downward oblique direction along the surface. Hence, the water adhering to the surface is also pushed by the flow of air as well as by gravity, thus advancing in a down oblique direction over the surface. Accordingly, the water adhering to the surface can be caused to drop efficiently.

In the gas detector according to any one of the detectors set forth, the chamber formed from the wall preferably constitutes a plate-like chamber whose dimension in a direction orthogonal to a direction in which the entrance of the chamber is connected to the exit of the chamber, with respect to a horizontal direction, is smaller than a distance between the entrance of the chamber and the exit of the same and smaller than a vertical dimension of the chamber; and the air vent is preferably formed in a side wall surface of the wall surface of the chamber in a direction in which the entrance of the chamber is connected to the exit of the same.

In the gas detector of the invention, the chamber assumes the shape of a plate-like chamber (space). Further, an air vent is formed in the sidewall surface extending in the direction in which the entrance and the exit of the chamber are connected together; for example, the side wall surface which is parallel to the direction in which the entrance and exit of the chamber are connected together. Specifically, the air vent is formed in the side wall surface orthogonal to the thicknesswise direction of the plate-like chamber. By means of such a construction, the volume of the chamber can be reduced. Hence, the air in the chamber can be replaced immediately. Further, the volume of the chamber opposing the air vent (i.e., the thicknesswise portion of the chamber) can be reduced. Hence, replacement of the air located in the vicinity of that area becomes faster. Therefore, when compared with a gas sensor provided in a chamber having a larger thicknesswise dimension, the gas sensor can be made relatively faster in response.

Moreover, according to the gas detector of the invention, the chamber is a plate-like chamber. Hence, the profile of the gas detector can be reduced.

BRIEF DESCRIPTION OF THE DRAWINGS

FIG. 1A is a front view of a gas detector according to an embodiment, and

FIG. 1B is a rear view of the same;

FIG. 3A is a front view of the gas detector of the embodiment when a substrate 170 having a gas sensor 180 mounted thereon is attached to a case main body 110, FIG. 3B is a front view of a center cover 150, and FIG. 3C is a front view of a cover 160;

DETAILED DESCRIPTION OF THE PREFERRED EMBODIMENTS

Figure 2:
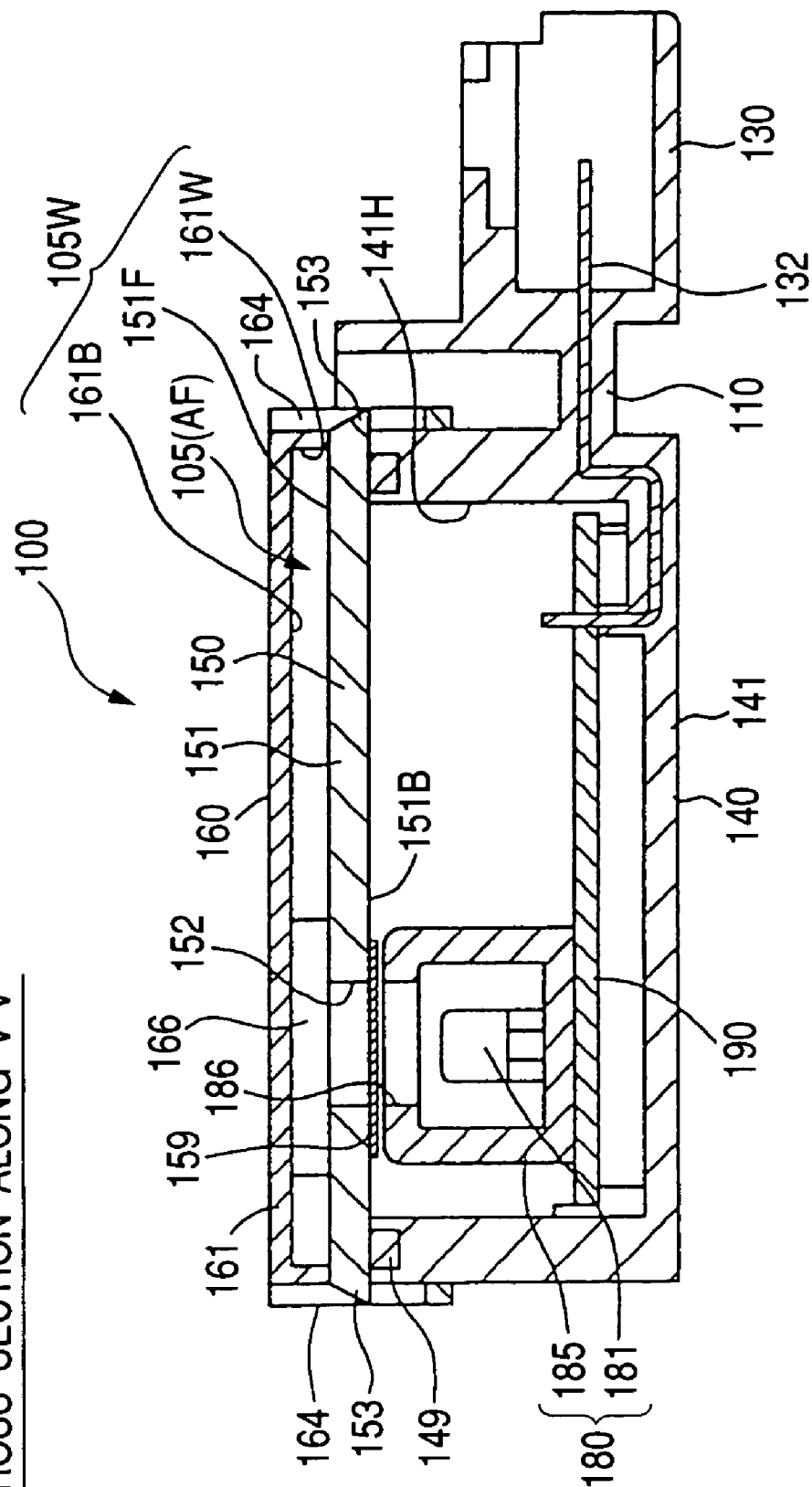
FIG. 2 is a cross-sectional view of the gas detector of the embodiment taken along line V–V'.

By reference to FIGS. 1 through 9, an embodiment of the invention will be described. A gas detector of the embodiment 100 comprises a case main body 110 (see FIG. 3A), a middle cover 150 (see FIG. 3B), a case 170 formed from a cover 160 (see FIG. 3C), and a wiring board 190 which is retained in the case 170 and has a gas sensor 180 (see FIG. 2). The case main body 110 of the case 170 has a bracket section 120 to be used for attaching the case 170 to another member (not shown); a connector section 130 on which are provided connectors (not shown) to be used for electrically connecting the wiring board 190 and the gas sensor 180 to the outside; and a main body section 140 for housing the wiring board 190. As shown in a front view of FIG. 1A, the gas detector 100 is used and attached to a vehicle body through use of mount holes 121 of the bracket section 120 such that the connector section 130 of the case 170 is placed at an elevated position with respect to a vertical direction and such that the bracket section 120 is placed on the right side when viewed from the front of the vehicle. Therefore, when the vehicle travels forward, air (wind) hits the front of the case 170 (i.e., from the viewer in the direction distant from the viewer in FIG. 1A).

Of the case main body 110 (see FIG. 3A), the main body section 140 has a substrate retaining section 141 having a substantially C-shaped cross-sectional profile and a substrate retaining recess section 141H for retaining the wiring board 190 therein. As shown in FIG. 2, A lead member 132 is connected and fastened to the wiring board 190 having the gas sensor 180 mounted thereon, by means of soldering. The lead member 132 is bent and arranged such that one end of the lead member 132 projects to the inside of the connector section 130.

Figure 5:
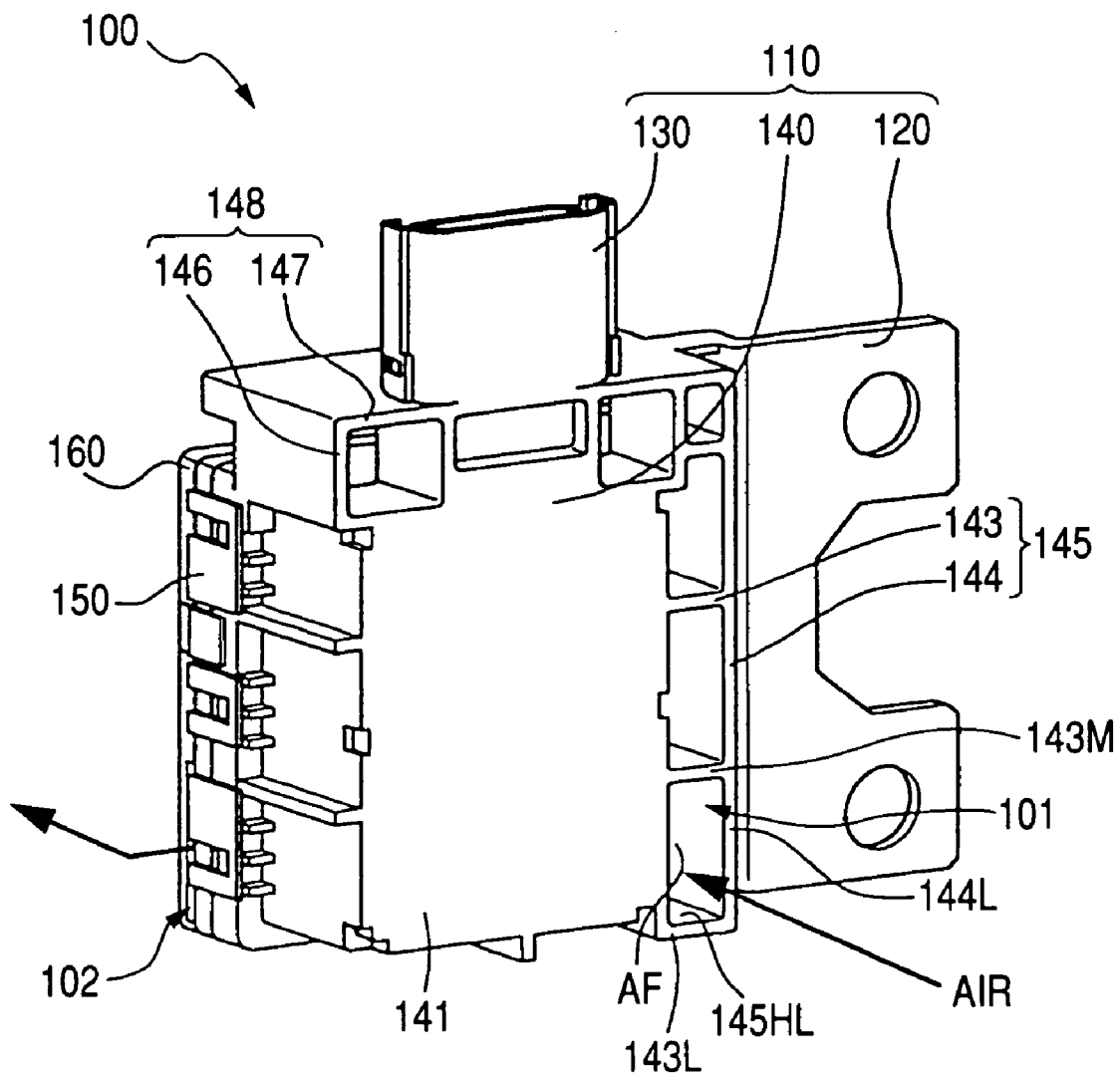
FIG. 5 is a perspective view of the gas detector of the embodiment when viewed from the front.

As shown in FIG. 3, the main body section 140 also comprises a bracket connection section 145 for connecting the substrate retaining section 141 to the bracket section 120; and a connector connection section 148 for connecting the substrate retaining section 141 to the connector section 130. Specifically, of these elements, the bracket connection section 145 is specifically constituted of a wall section 144 spaced from the substrate retaining section 141, and a coupling section 143 for coupling the substrate retaining section 141 to the wall section 144. The area surrounded by these elements constitute a through hole 145H which penetrates through the front and back of the case main body 110. As shown in FIG. 5, a lower through hole 145HL surrounded by a lower section 144L, belonging to the substrate retaining section 141 and the wall section 155, and coupling sections 143L, 143M constitute an air inlet port 101 for taking in the air that hits the front surface of the case 170 and serve as a part of an air flow channel AF.

The connector connection section 148 is also specifically constituted of a wall section 147 spaced from the substrate retaining section 141; and a coupling section 146 for coupling the substrate retaining section 141 to the wall section 147.

The gas sensor 180 includes one or a plurality of gas sensor elements 181 capable of sensing either a change in the concentration of oxidizing gas such as NOx or a change in the concentration of reducing gas such as CO or HC (hydrocarbon), or both concentrations. The gas sensor 180 has a structure for enclosing the gas sensor element 181 (see FIG. 2). A sensor cover air vent 186 is formed in a sensor cover 185, thereby enabling taking in of external air into the sensor cover 185. In addition to including the gas sensor 180, the wiring board 190 has unillustrated electronic components such as a microcomputer, capacitors, and resistors. Accordingly, a signal output from the gas sensor element 181 provided in the gas sensor 180 by means of the electronic components. Information about a change in the concentration of target gas (i.e., the oxidizing gas or the reducing gas) is output to the outside by way of the lead member 132.

As shown in FIG. 2, in order to protect the gas sensor 180 and the wiring board 190, the center cover 150 is fitted into the substrate retaining section 141 of the main body section 140 by way of an O ring 149. As shown in FIG. 3B, the center cover 150 is a plate-like member having a substantially-rectangular shape when viewed from the front. Center cover engagement sections 154 formed so as to project from the side of the center cover main body 151 engage with center cover lock claws 142 formed at positions on the side surface of the substrate retaining section 141, whereby the center cover 150 is attached to the main body section 140.

Another air vent 152 is formed in the center cover main body 151 at a position overlapping the center cover air vent 186 of the gas sensor 180 when viewed from the front. As shown in FIG. 2, a filter member 159 having the characteristic of enabling passage of air and gas but preventing passage of water droplets is affixed to a center cover back wall surface 151B of the center cover main body 151 so as to cover the air vent 152. Because of the filter, gas, such as air, can penetrate through a space between a center cover front wall surface 151F of the center cover main body 151 and the inside of the gas sensor 180; that is, the gas sensor element 181, by way of the air vent 152 and the sensor cover air vent 186.

Figure 4:
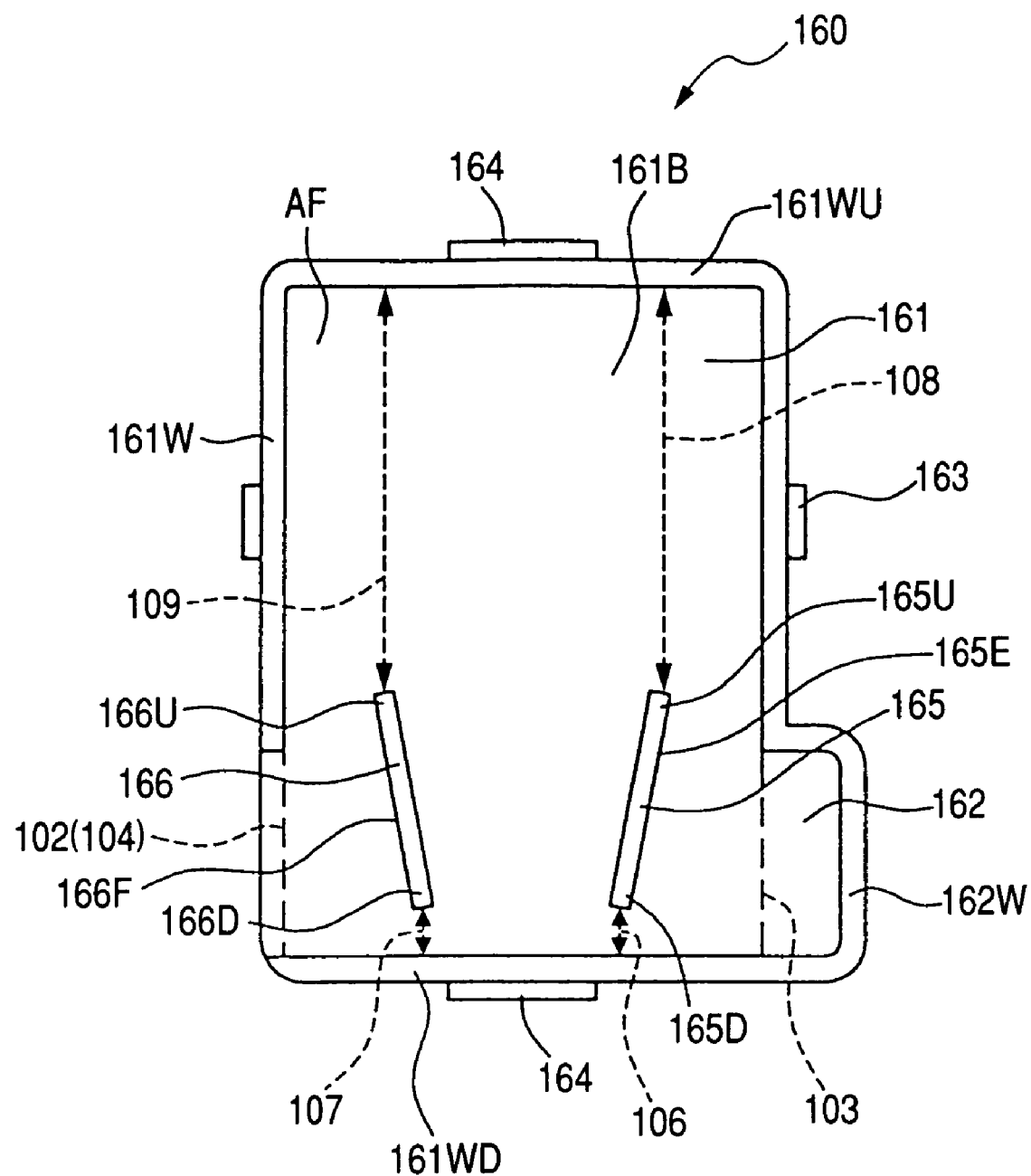
FIG. 4 is a rear view of the gas detector of the embodiment when viewed from the front.

In order to make a chamber 105, which constitutes a part of the flow channel AF as will be described later, a cover 160 is fitted to the center cover 150. As shown in FIGS. 3C and 4, the cover 160 is a plate-like member having a substantially-rectangular shape when viewed from the front. Cover engagement sections 164 made so as to project from the side of the cover main body 161 engage with cover lock claws 153 formed on upper and lower side surfaces of the center cover main body 150, whereby the cover 160 is attached to the main body section 140 by way of the center cover 150. Cover retaining sections 163 projecting from the sides of the cover main body 161 do not engage with the cover lock claws 153 but retain the center cover main body 151 and the cover main body 161 in proper positions.

The cover 160 also has a cover bulge section 162, which bulges sideways, in a lower left portion of the cover when viewed from the front (see FIG. 3C). The cover 160 further has a cover circumferential wall section 161W, which projects toward the cover back wall surface 161B, over substantially the entire circumference of the cover except for a part thereof. When the cover 160 is attached to the center cover 150, the cover circumferential wall section 161W comes into contact with the center cover front wall surface 151F of the center cover main body 151 (see FIG. 2). Accordingly, as shown in FIG. 2, a space, i.e., the chamber 105, is defined between the cover back wall surface 161B of the cover 160 and the center cover front wall surface 151F of the center cover main body 151, by means of a chamber wall surface 105W formed from the cover circumferential wall section 161W.

When the cover 160 is attached to the main body section 140 by way of the center cover 150, the cover bulge section 162 is arranged so as to cover the lower through hole 145HL from the back. Hence, the back side of the lower through hole 145HL is closed by the cover bulge section 162 (see FIG. 1B), and the lower through hole 145HL is connected to the chamber 105.

A lower left portion of the circumference of the cover 160 is not provided with the cover circumferential wall section 161W, thereby constituting a chamber exit 104. Hence, the air that has flowed into the chamber 105 from a chamber entrance 103 of the cover bulge section 162 is discharged from the chamber exit 104.

Figure 6:
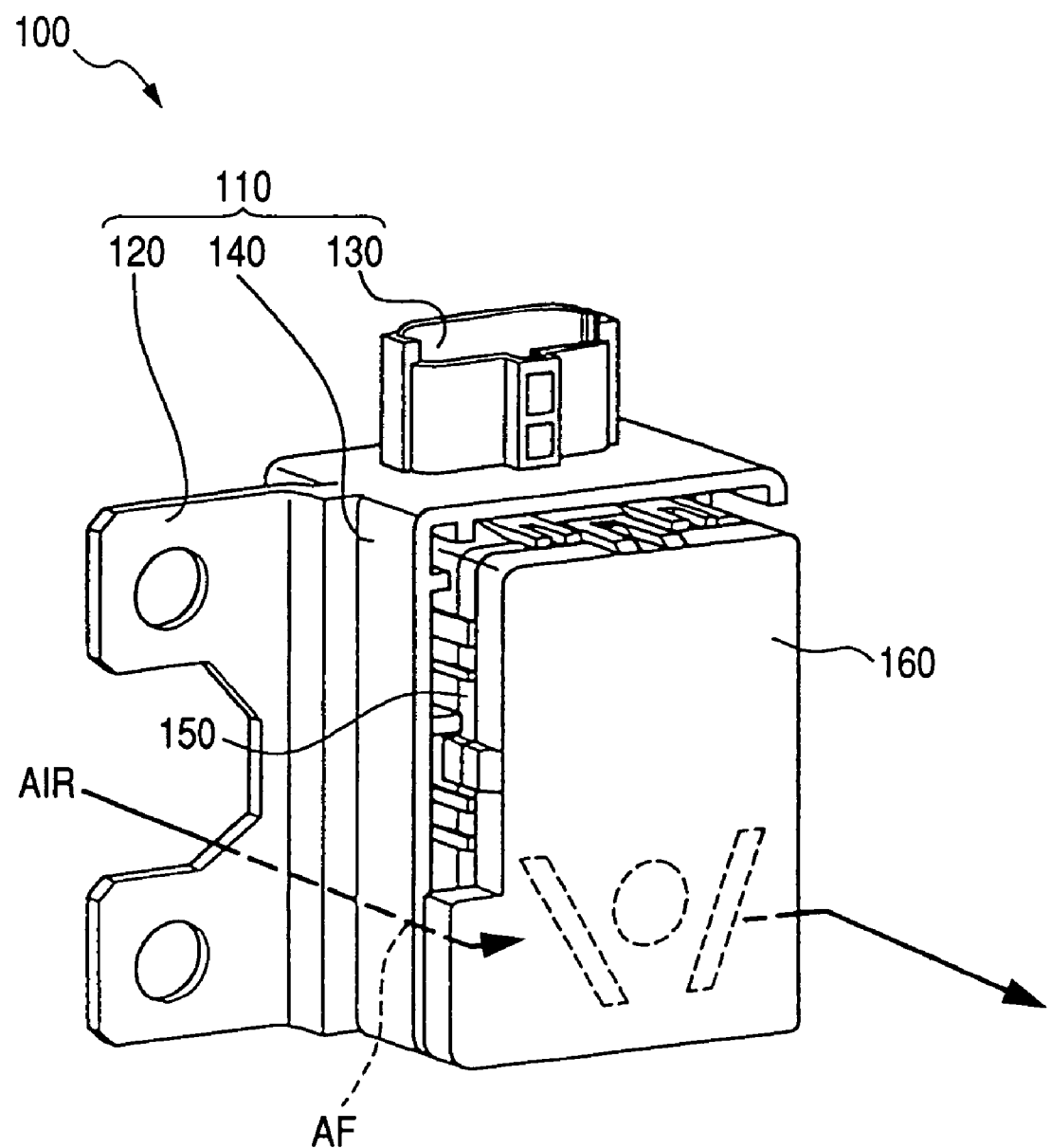
FIG. 6 is a perspective view of the gas detector according to the embodiment when viewed from the rear.
Figure 7:
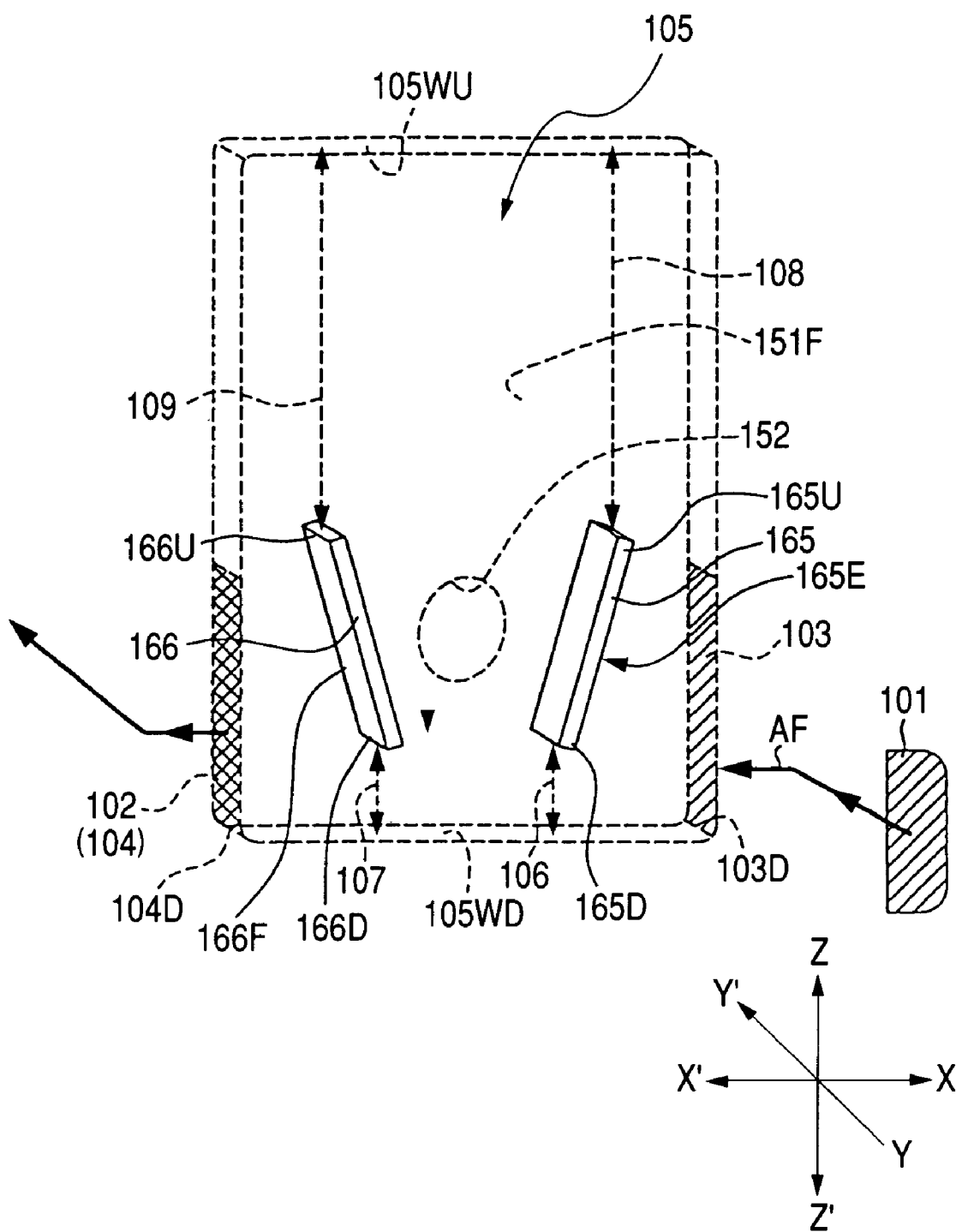
FIG. 7 is a perspective descriptive view of the inside of a gas detector 105 of the embodiment.

As indicated by the arrows shown in FIGS. 5, 6, and 7, as the vehicle travels forward, the air approaching the front surface of the gas detector 100 flows into an air flow channel AF. Specifically, air enters the lower through hole 145HL from the air inlet port 101 and comes into collision with the cover bulge section 162 of the cover 160, thereby shifting direction. Subsequently, the air passes through the chamber entrance 103 and enters the chamber 105 (see FIG. 7). After having proceeded through the chamber 105, the air is discharged from the chamber exit 104. In the embodiment, no flow channel is present in the area downstream from the chamber exit 104. Further, the chamber exit 104 constitutes a part of the opening edge of the bottom wall section 161WD of the cover circumferential wall section 161W constituting the bottom section.

Of the cover back surface 161B of the cover main body 161, a first shielding plate 165 and a second shielding plate 166, which are substantially identical in thickness with the cover circumferential wall section 161W, are formed projectingly at positions slightly below the center of the cover back surface (see FIG. 4).

Further, the first shielding plate 165 is arranged so as not to come into contact with the cover circumferential section 161W. Specifically, of the cover circumferential wall section 161W, a first lower gap 106 is formed between the bottom wall section 161WD situated at the bottom section and a lower end 165D of the first shielding plate 165, as indicated by a broken arrow shown in FIG. 4. Of the cover circumferential wall section 161W, a first upper gap 108 is formed between an upper wall section 161WU located at an upper position and an upper end 165U of the first shielding plate 165. As can be seen from FIG. 4, an entrance-opposed surface 165E, which opposes the chamber entrance 103, is formed on the first shielding plate 165 so as to be oriented in a downward oblique direction (i.e., a right lower direction in the drawing).

Figure 8:
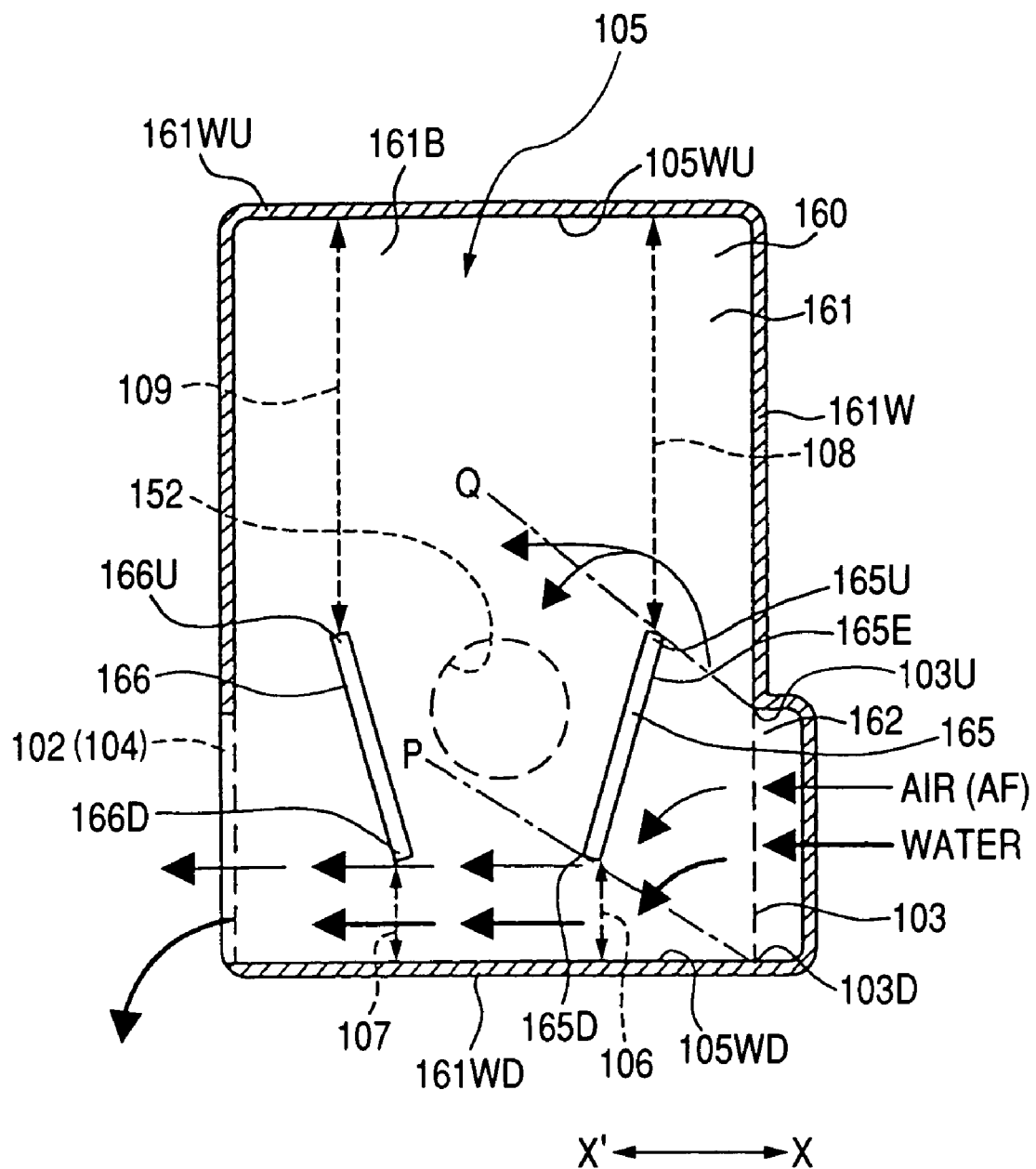
FIG. 8 is a descriptive view of the chamber 105 of the gas detector of the embodiment when viewed from the front, showing the flow of air and water that have entered into the chamber 105 from a chamber entrance 103.

As indicated by a dashed line in FIG. 8, an imaginary line P is drawn so as to connect a lower end 103D of the chamber entrance 103 to a lower end 165D of the first shielding plate 165 and to extend toward the chamber exit (i.e., the left side of the drawing). Another imaginary line Q is drawn so as to connect an upper end 103U of the chamber entrance 103 to an upper end 165U of the first shielding plate 165 so as to extend toward the chamber exit (i.e., the left side of the drawing). Then, the first shielding plate 165 is arranged such that the air vent 152 indicated by broken lines is situated between the lines P and Q. Consequently, when viewed from the entrance 103, the first shielding plate 165 is arranged such that the air vent 152 is concealed.

Likewise, the second shielding plate 166 is also arranged so as not to come into contact with the cover circumferential wall section 161W. Specifically, a second lower gap 107 is formed between the bottom wall section 161WD situated at the bottom section and a lower end 166D of the second shielding plate 166. Further, a second upper gap 109 is formed between the upper wall section 161WU and the upper end 166U of the second shielding plate 166. As can be seen from FIG. 4, the second shielding plate 166 is formed such that an exit-opposed surface 166F, which opposes the chamber exit 104, is oriented in an oblique downward direction (i.e., a lower left direction in the drawing).

Figure 9:
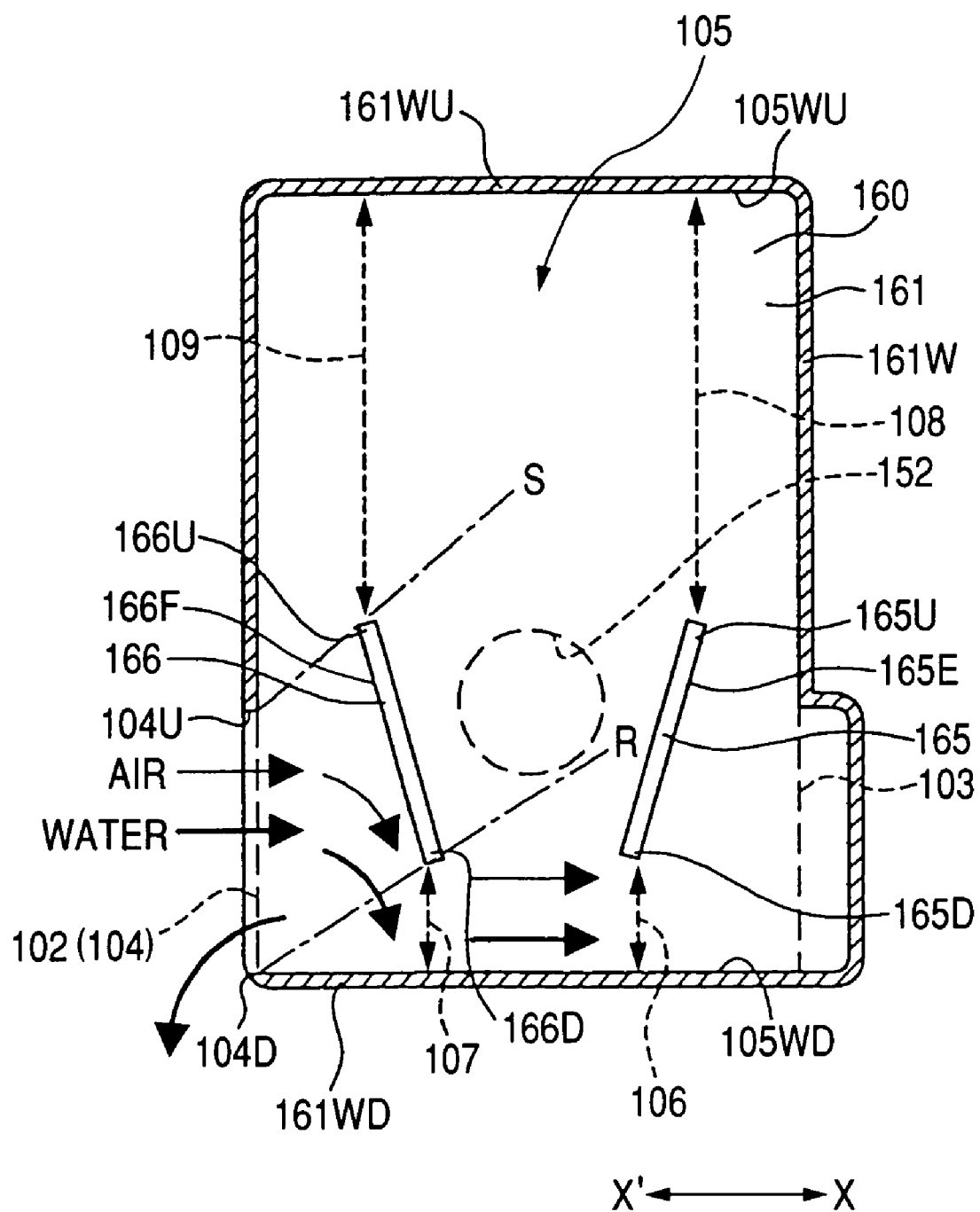
FIG. 9 is a descriptive view of the chamber 105 of the gas detector of the embodiment when viewed from the front, showing the flow of air and water that have entered the chamber 105 from a chamber exit 104 (i.e., an air outlet port 102) through backflow.

As indicated by a dashed line shown in FIG. 9, an imaginary line R is drawn so as to connect a lower end 104D of the chamber exit 104 to a lower end 166D of the second shielding plate 166 and extend toward the entrance of the chamber (i.e., the right side in the drawing). Another imaginary line S is drawn so as to connect an upper end 104U of the chamber entrance 104 to an upper end 166U of the second shielding plate 166 and to extend toward the entrance of the chamber (i.e., the right side in the drawing). Then, the air vent 152 indicated by broken lines is situated between the lines R and S. Consequently, the second shielding plate 166 is arranged such that the air vent 152 is concealed when viewed from the exit 104 of the chamber.

In this way, the first shielding plate 165 and the second shielding plate 166 are formed within the chamber 105 (see FIG. 7). Further, the air vent 152 remaining in communication with the gas sensor 180 is opened at a position higher than the bottom wall section 161WD between the first shielding plate 165 and the second shielding plate 166. As shown in FIGS. 7 and 8, a bottom wall surface 105WD of the chamber 105, which is constituted of the bottom wall section 161WD of the cover circumferential wall section 161W, constitutes a horizontal surface. The lower end 103D of the chamber entrance 103 is flush with the lower end 104D of the chamber exit 104.

There will now be described flow of air in the chamber 105, flow of water droplets that have entered the chamber along with air, and gas sensing operation of the gas sensor 180. As shown in FIG. 7, the air that has entered into the air inlet port 101 as the vehicle travels proceeds in a Y–Y' direction (i.e., a direction distant from the viewer in the drawing) and then has a turn and advances in a X–X' direction (i.e., a leftward direction in the drawing). The air then enters the chamber 105 by way of the chamber entrance 103. The air 105 is a rectangular small space which is smaller in dimension in the Y–Y' direction orthogonal to the X–X' direction, in which the chamber entrance 103 is connected to the chamber exit 104, and a Z–Z' direction (i.e., a vertical direction) than in the X–X' direction and the Y–Y' direction. The air vent 152 is formed in the center cover front wall surface 151F extending in the X–X' direction.

The width of the first shielding plate 165 and that of the second shielding plate 166 (i.e., the dimensions of the first and second shielding plates in the Y–Y' direction) are substantially identical with the thickness of the chamber 105. Hence, the air that has proceeded in the X–X' direction shifts direction when hitting the entrance-opposed surface 165E of the first shielding plate 165, as indicated by a fine line shown in FIG. 8. More specifically, the entrance-opposed surface 165E has such a shape as to become far distant from the chamber entrance 103 as approaching the lower end 165D of the first shielding plate 165. In short, the entrance-opposed surface 165E is tilt downwardly, and hence most of the air that has entered the chamber entrance 103 proceeds in a downward oblique direction (i.e., a lower left direction in FIG. 8) along the entrance-opposed surface 165E. The air passes through the first lower gap 106 and the second lower gap 107, proceeds in the X–X' direction along the bottom wall section 161WD, and is discharged from the chamber exit 104.

The gas detector 100 is attached to the rear of a front grill, and hence a large quantity of fog-like or grain-like water droplet sometimes flow into the air flow channel AF along with air when the vehicle travels in rain. In such a case, the water droplets that have advanced through the air flow channel AF, specifically, the through hole 145HL along with air come into collision with the cover bulge section 162 and adhere to the wall surface and drop down. Further, the water droplets that have shifted direction toward a sideway direction along with air enter the chamber 105 by way of the chamber entrance 103, as indicated by a bold arrow shown in FIG. 8, thereby coming into collision with and adhering to the entrance-opposed surface 165E of the first shielding plate 165. As mentioned previously, the first shielding plate 165 is arranged such that the air vent 152 is concealed when viewed from the chamber entrance 103. Therefore, the water droplets that have entered the chamber 105 by way of the chamber entrance 103 do not directly arrive at the air vent 152.

The water adhering to the entrance-opposed surface 165E is pushed by the air flowing along the entrance-opposed surface 165E as well as by gravity, thus advancing downwardly. The water then drips downward and is accumulated on the bottom wall surface 105WD that is an upper surface of the bottom wall section 161WD. Further, the water is pushed by the flow of air, to thereby advance to the chamber exit 104. The water is then discharged downward from the chamber exit 104. Specifically, the water that has entered the chamber 105 proceeds in the same direction as that in which air flows and is pushed to advance by the air. Hence, in contrast with a structure in which water returns to and is discharged from the entrance, accumulation of water does not close or hinder the flow of air. Accordingly, even when air containing a large quantity of water droplets has flowed into the gas detector, water and air can be discharged smoothly, thereby ensuring smooth circulation of air. Particularly, the bottom wall surface 105WD of the chamber 105 constitutes a part of the opening edge of the chamber exit 104. Hence, discharge of water from the chamber exit 104 is easy.

Since the air vent 152 is situated at a position higher than the bottom wall surface section 161WD, the water does not intrude into the air vent 152 even when water is accumulated on or flows over the bottom wall surface 105WD.

Further, according to the embodiment, the first upper gap 108 is also formed between the upper wall section 161WU and the upper end 165U of the first shielding plate 165. Hence, as indicated by the fine arrow shown in FIG. 8, a portion of the air that has flowed from the chamber entrance 103 goes upward and proceeds in the X–X' direction (i.e., the leftward direction in the drawing) or the lower left direction in the drawing, by way of the first upper gap 108. Therefore, the air existing in the vicinity of the air vent 152 can be exchanged readily. Hence, a change in the oxidizing and reducing gases contained in air can be detected by the gas sensor 180 more quickly. Specifically, the response of the gas sensor 180 can be made quick. In particular, according to the embodiment, the chamber 105 is formed into the shape of a plate which is thin (has a small dimension) in the direction Y–Y'. Hence, the quantity of air existing in front of the air vent 152 can be relatively reduced. Accordingly, exchange of a small quantity of air enables reflection of a gas concentration which is a current object of measurement. Therefore, the response of the gas sensor 180 can be made particularly fast.

When air is blown from backward when the vehicle is stationary or when water droplets come from backward as in the case of car wash, air or water droplets sometimes flow backwardly from the chamber exit 104 (i.e., the air outlet port 102) and intrude into the chamber 105.

In this case, the air that has advanced in the X'–X direction (i.e., a rightward direction) hits the exit-opposed surface 166F of the second shielding plate 166. The exit-opposed surface 166F has such a shape that the exit-opposed surface 166F becomes far distant from the chamber exit 104 as approaching to the lower end 166D of the second shielding plate 166. More specifically, the exit-opposed surface is oriented obliquely downward, and hence most of the air that has entered the chamber from the chamber exit 104 proceed in an oblique downward direction (i.e., a lower right direction in FIG. 9) along the exit-opposed surface 166F, as indicated by a fine arrow in FIG. 9. The air also advances so as to pass through the second lower gap 107 and the first lower gap 106 and is discharged from the chamber entrance 103 and the air inlet port 101.

The water droplets that has advanced in the direction X'–X (i.e., the rightward direction in the drawing) come into collision with and adhere to the exit-opposed surface 166F of the second shielding plate 166. As mentioned previously, the second shielding plate 166 is arranged such that the air vent 152 is concealed when viewed from the chamber exit 104. Therefore, the water droplets that have entered the chamber 105 through the chamber exit 104 are prevented from directly reaching the air vent 152. The water is pushed by the air that flows along the exit-opposed surface 166F as well as by gravity proceeds downwardly and drips downward. The water is then accumulated on the bottom wall surface 105WD that is the upper surface of the bottom wall section 161WD. Further, the water is pushed by the air and proceeds to the chamber entrance 103. The water is discharged from the chamber entrance 103 and also from the air inlet port 101. In this way, the water droplets that have entered the chamber 105 are smoothly discharged. Thus, accumulation of water in the chamber 105 and subsequent intrusion of water into the gas sensor 180 are prevented.

The second upper gap 109 is formed also between the upper wall section 161WU and the upper end 166U of the second shielding plate 166. Therefore, a portion of the water that has entered the chamber (flowed backward) from the chamber exit 104 proceeds upwardly and passes through the second upper gap 108. The portion of the water then advances in the X'–X direction (i.e., the rightward in the drawing) or a lower right direction in the drawing. Therefore, the air existing in the vicinity of the air vent 152 can be replaced readily.

In this way, in the case of the gas detector 100 of the embodiment, even when water droplets have intruded into the air flow channel AF, particularly into the chamber 105, along with air, the water droplets are prevented from being poured directly on the air vent 152. Water can be discharged appropriately along with air and also by utilization of air. Hence, water is not accumulated in the chamber 105, and an air flow channel can also be ensured.

There will now be described manufacture of the gas detector 100 of the embodiment. Any of the case main body 110 constituting the case 170, the center cover 150, and the cover 160, all belonging to the gas detector 100, are formed from PBT (Polybutene Terephthalate) into which about 30 wt. % of glass fiber is mixed and formed by means of the known injection molding technique. The wiring board 190 is formed from glass-epoxy resin complex material. Electronic components such as a microcomputer and resistors as well as the gas sensor 180 are mounted on the wiring board 190 by means of soldering. The wiring board 190 is disposed in the board retaining recess section 141H of the main body section 140. The lead member 132 is soldered to the wiring board 190, whereby the wiring board 190 is fixed to the inside of the board retaining recess section 141H. Subsequently, the wiring board 190 and the board retaining recess section 141H are fitted together such that the center cover lock claws 142 engage with the center cover engagement sections 154 and also such that the cover lock claws 153 engage with the cover engagement sections 164. Thereby, the chamber 105 is made between the center cover 150 and the cover 160. Finally, the gas detector 100 is completed.

First Modification

An overview of a first modification will now be described by reference to FIG. 10. In the above embodiment, the cover 160 is a plate-like member having a substantially rectangular shape when viewed from the front (see FIGS. 3C and 4). The bottom wall surface 105WD of the chamber 105 constitutes a horizontal surface, and the lower end 103D of the chamber entrance 103 is flush with the lower end 104D of the chamber exit 104.

Figure 10:
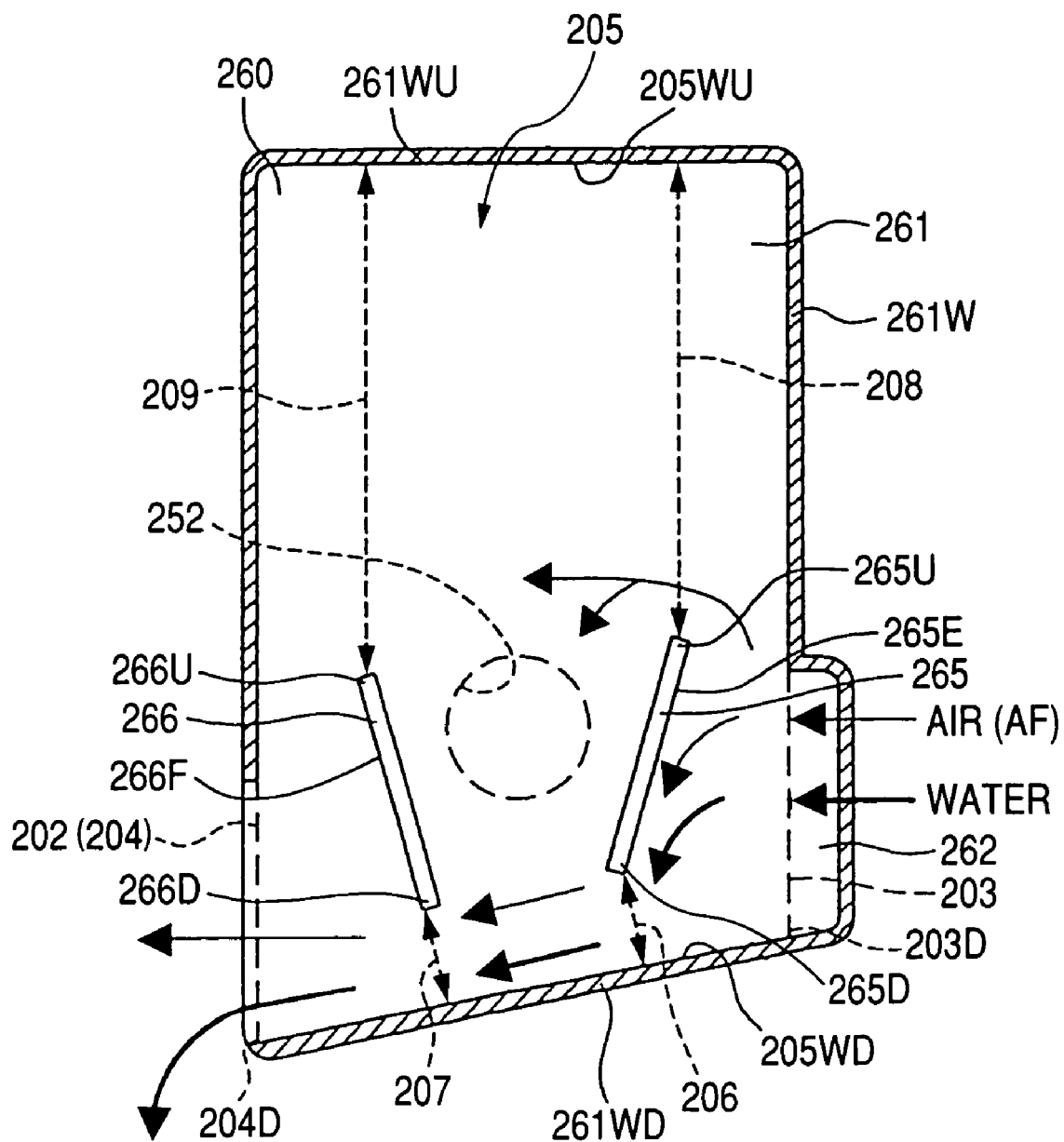
FIG. 10 is a descriptive view of a chamber 205 of the gas detector of a first modification when viewed from the front, showing the flow of air and water that have entered into the chamber 205 from a chamber entrance 203.

As shown in FIG. 10, in the first modification, a bottom wall section 261D constituting a bottom section of the cover circumferential wall section 261W formed along the circumference of the cover 260 is inclined such that a left portion of the cover becomes lower than a right portion of the same. A bottom wall surface 205WD of a chamber wall surface 205W constituting a chamber 205 also assumes a shape such that a portion of the wall surface 205WD facing the chamber exit 204 becomes lower than a portion of the same facing the chamber entrance 203. Further, a lower end 204D of the chamber exit 204 is situated lower than a lower end 203D of a chamber entrance 203.

The air that has flowed into the chamber from the chamber entrance 203 located close to a cover bulge 262 hits an entrance-opposed surface 265E of the first shielding plate 265. Most of the air proceeds in an oblique downward direction (i.e., a lower left direction in the drawing) along the entrance-opposed surface 265E, as indicated by a fine arrow shown in FIG. 10. The air passes through a first lower gap 206 and a second lower gap 207 in an oblique, left downward direction along the bottom wall section 261WD and is discharged from the chamber exit 204.

The water droplets that have entered the chamber 205 by way of the chamber entrance 203 along with air hit and adhere to the entrance-opposed surface 265E of the first shielding plate 265, as indicated by a bold arrow shown in FIG. 10. the first shielding plate 265 is also arranged so as to conceal the air vent 252 when viewed from the chamber entrance 203. Hence, water droplets do not directly reach the air vent 252. The water that has adhered to the entrance-opposed surface 265E is pushed by the air that flows along the entrance-opposed surface 265E as well as by gravity, thereby proceeding downward. The water than drips onto the bottom wall surface 205WD. The water is pushed by the air flow, to thereby proceed toward the chamber exit 204 under influence of gravity. Specifically, in contrast with the embodiment, the water that has been accumulated on the bottom wall surface 205WD is also sent to the chamber exit 204 under the influence of gravity, because the bottom wall surface 205WD is inclined toward the chamber exit 204. By means of such a construction, air and water can be discharged more smoothly than the embodiment, thus ensuring smooth circulation of air. Here, the bottom wall surface 205WD of the chamber 205 is utilized as a part of the opening edge of the chamber exit 204. Hence, the first modification is analogous to the embodiment in that discharge of water from the chamber exit 204 is easy.

Even in the first modification, a second shield plate 266 is employed. Hence, even when air or water droplets have entered the chamber 205 from the chamber exit 204, the water droplets do not arrive directly at the air vent 252.

Further, even the first modification employs the first upper gap 208 and the second upper gap 209. Hence, the air existing in the vicinity of the air vent 252 can be readily exchanged, and response of the gas sensor 180 can be made quick.

In the first modification, only the shape of the cover 260 is disclosed. However, needless to say, the shape of the center cover or that of the case main body (i.e., a main body section) may be changed so as to conform with the shape of the bottom wall section 261WD of the cover circumferential wall section 261W.

Second Modification

There will now be described an overview of a second modification by reference to FIG. 11. In the embodiment, the cover bulge section 162 of the cover 160 is provided at a lower position on the side thereof (see FIGS. 3C and 4). The lower end 103D of the chamber entrance 103 is identical in height with the lower end 104D of the chamber exit 104.

Figure 11:
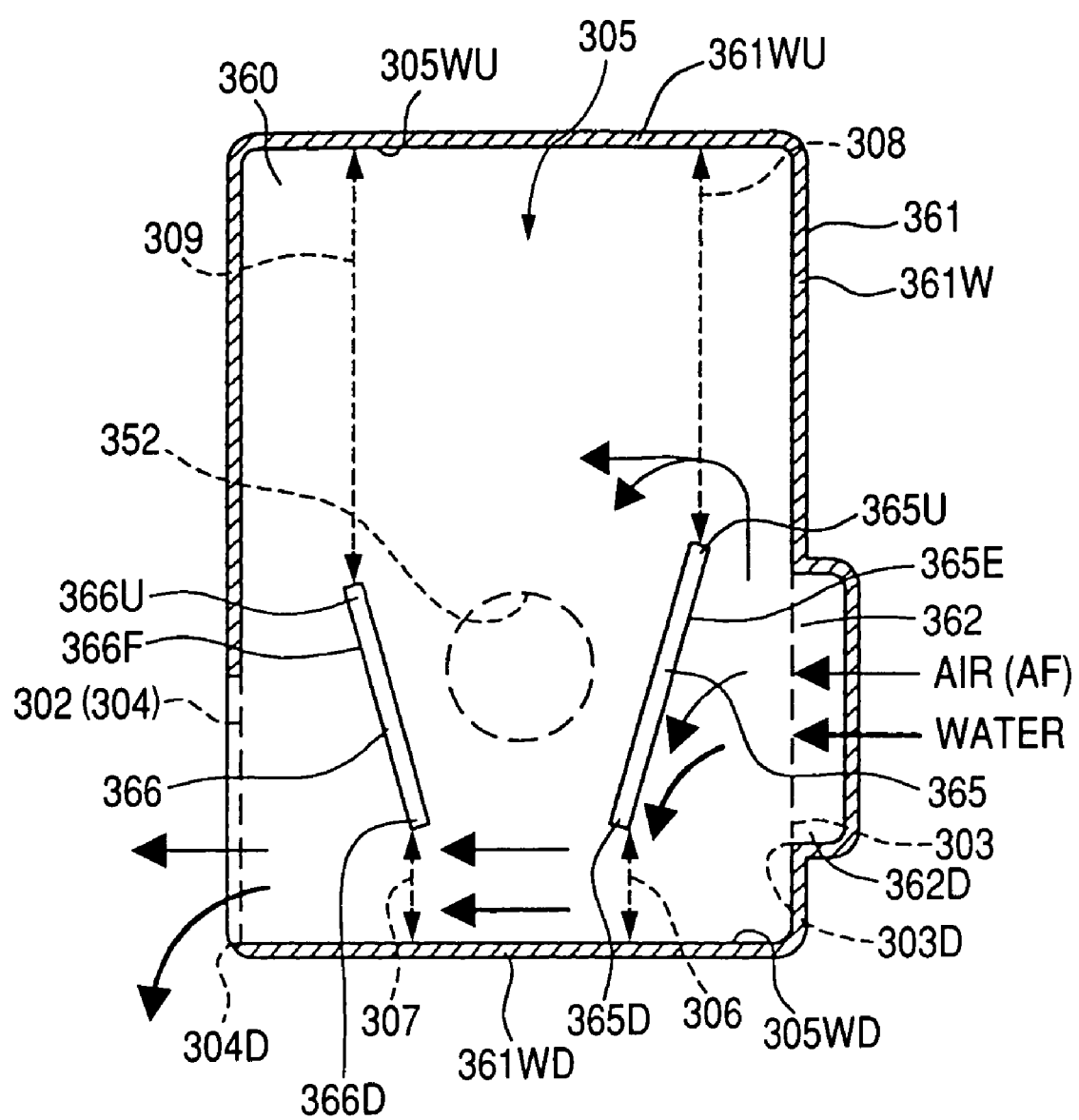
FIG. 11 is a descriptive view of a chamber 305 of the gas detector of a second modification when viewed from the front, showing the flow of air and water that have entered into the chamber 305 from a chamber entrance 303.

As shown in FIG. 11, according to the second embodiment, the cover bulge section 362 formed on the side of the cover 360, particularly the lower end 362D, is situated higher than the bottom wall section 361D of the cover circumferential wall section 361W. Hence, the lower end 304D of the chamber exit 304 is situated lower than the lower end 303D of the chamber entrance 303.

The air that has flowed into the chamber from the chamber entrance 303 of the cover bulge section 362 hits the entrance-opposed surface 365E of the first shielding plate 365. Most of the air goes in an oblique downward direction (i.e., a lower left direction in the drawing) along the entrance-opposed surface 365E, as indicated by a fine arrow shown in FIG. 11. The air passes through the first lower gap 306 and the second lower gap 307 and advances left along the bottom wall section 361WD. The air is then discharged from the chamber exit 304.

The water droplets that have entered the chamber 305 along with air by way of the chamber entrance 303 hit the entrance-opposed surface 365E of the first shielding plate 365, as indicated by a bold arrow shown in FIG. 11. The water droplets then adhere to the entrance-opposed surface and are pushed by the air flowing along the entrance-opposed surface 365E and gravity. Thus, the water droplets go downward and drip and are accumulated on the bottom wall surface 305WD. The first shielding plate 365 is also arranged so as to conceal the air vent 352 when viewed from the chamber entrance 303. Therefore, the water droplets fail to directly arrive at the air vent 352. The water accumulated on the bottom wall surface 305WD is pushed by the air flow, to thereby advance toward the chamber exit 304. The water is then drained downward from the chamber exit 304.

In the second modification, the chamber entrance 303, particularly the lower end 303D of the chamber entrance, is situated higher than the bottom wall surface 305WD of the chamber 305. Hence, even when a large quantity of water is accumulated on the bottom wall surface 305WD, the water is prevented from exceeding the chamber entrance 303 and returning to an upstream of the air flow channel AF. Therefore, water flows in the direction opposite the flowing direction of air (i.e., the direction of the flow channel). Thereby, a decrease in circulation of air, which would otherwise be caused when water closes the air flow channel, is prevented.

Since the second modification also employs the second shielding plate 366, water droplets do not directly reach the air vent 352 even when the air or water droplets flow backward from the chamber exit 304 and intrude into the chamber 305.

Further, the second modification also has the first upper gap 308 and the second upper gap 309. Hence, the air existing in the vicinity of the air vent 352 can be exchanged readily, and response of the gas sensor 180 can be made fast.

Although the second modification shows only the shape of the cover 360. However, needless to say, the shape of the center cover or that of the case main body (i.e., the main body section) can also be changed so as to conform to the shape of the bottom wall section 361WD of the cover circumferential wall section 361W.

Up to this point, the invention has been described by reference to the embodiment and the first and second modifications. However, the invention is not limited to the embodiment. Needless to say, the invention can be applied while being modified within the scope of the invention.

For instance, the embodiment has shown that the flow channel AF (i.e., the lower through hole 145HL) is also present at a position higher than the chamber entrance 103 of the chamber 105 and that the flow channel AF ends at the chamber exit 104 of the chamber 105. However, the invention can also be applied to a gas detector in which a flow channel is also present at a position downstream of the chamber exit or a gas detector in which no flow channel is present at any location close to the chamber entrance.

When a flow channel is formed also in an area downstream of the chamber, it is better to make the bottom surface of the downstream flow channel lower than the lower end of the chamber exit such that back-flow of water from the chamber exit does not again return to the chamber.

The Y–Y' dimension of the first shielding plate 165 formed in the cover 160 and that of the second shielding plate 166 (see FIG. 7) are made substantially identical with that of the thicknesswise dimension (i.e., in the Y–Y' direction) of the chamber 105. However, the only requirement is to conceal the air vent when viewed from the chamber entrance. So long as the air vent is concealed, the Y–Y' dimension of the first shielding plate is made smaller than the thicknesswise direction (Y–Y' direction) of the chamber.

Although the gas sensor employing the gas sensor element (i.e., a gas sensing element) 181 provided in the sensor cover 185 has been employed as the gas sensor 180, a gas sensor element unit may also be employed.

There is also employed a structure such that the air vent 152 is formed in the center cover 150 and such that the gas sensor element 181 is in communication with the chamber 105 by way of the center cover air vent 186 of the sensor cover 185. However, the sensor cover 185 may also be employed so as to constitute a portion of the wall surface of the chamber 105. In place of the air vent 152, the sensor cover air vent 186 formed in the sensor cover 185 may also be utilized.

In the embodiment, the center cover 150 and the cover 160 are formed separately. However, the chamber 105 is constituted by combination of these elements. However, a chamber construction member that has the chamber 105, in which the entrance shield plate 165 and an exit shielding plate 166 are provided, and that has the center cover and the cover, both being assembled into a single piece, may also be formed by means of the known injection molding technique. Conversely, a chamber may be formed by combination of three or more of the members.

What is claimed is:

1. A gas detector comprising:
   a case having an interior wall surface constituting a flow channel therein, through which air flows; and
   a gas sensor which is disposed in the case and detects a change in the concentration of specific gas in the air flowing through the flow channel, wherein
   when the gas detector is disposed in a setup state, the case includes
   a chamber wall surface which constitutes a chamber occupying at least a portion of the flow channel belonging to the interior wall surface; and which includes a bottom wall surface for constituting a bottom surface of the chamber, a chamber entrance that is situated on a side of the chamber and opens toward an upstream portion of the flow channel, a chamber exit that is situated on a side of the chamber, opens toward a downstream portion of the flow channel, has a lower open edge remaining flush with or situated lower than the entrance of the chamber, and has a portion of the bottom wall surface taken as a portion of the open edge, and an air vent that is provided toward the exit of the chamber when viewed from the entrance of the chamber and at a position higher than the bottom wall surface and guides air to the gas sensor; and
   an entrance-side shielding member which is situated between the chamber entrance and the air vent, both belonging to the chamber; which shields the air vent when viewed from the entrance of the chamber; and which constitutes a first lower gap between the lowermost portion of the entrance-side shielding member and the bottom wall surface and circulates at least a portion of the air that has flowed into the chamber, and wherein
   the bottom wall surface constitutes a horizontal plane or assumes a plate-like shape which becomes lower as the bottom wall surface approaches the exit of the chamber.

2. The gas detector according to claim 1, wherein
   the wall surface of the chamber includes an upper wall surface constituting an upper surface of the plate-like chamber; and
   the entrance-side shielding member constitutes a first upper gap, through which at least a portion of the air having flowed into the chamber circulates, between the highest portion of the entrance-side shielding member and the upper wall surface.

3. The gas detector according to claim 1, wherein
   a surface of the entrance-side shielding member opposing the entrance of the chamber has a geometry that a lower portion of the surface becomes distant from the entrance of the chamber.

4. The gas detector according to claim 1, further comprising:
   an exit-side shielding member which is situated between the air vent of the chamber and the exit of the chamber; which shields the air vent when viewed from the exit of the chamber; and which constitutes a second lower gap between the lowermost section of the exit-side shielding member and the bottom wall surface and through which at least the air having flowed into the chamber circulates.

5. The gas detector according to claim 1, wherein
   a surface of the exit-side shielding member opposing the exit of the chamber has a geometry that a lower portion becomes distant from the exit of the chamber.

6. The gas detector according to claim 1, wherein
   the chamber formed from the wall constitutes a plate-like chamber whose dimension in a direction orthogonal to a direction in which the entrance of the chamber is connected to the exit of the chamber, with respect to a horizontal direction, is smaller than a distance between the entrance of the chamber and the exit of the same and smaller than a vertical dimension of the chamber; and
   the air vent is formed in a side wall surface of the wall surface of the chamber in a direction in which the entrance of the chamber is connected to the exit of the same.

7. The gas detector according to claim 1, wherein
   at least either the gas-sensor-side air vent or the opposite-side air vent of the air vents is coated with a filtering material which enables circulation of air but prevents circulation of water droplets.

* * * * *